US012589251B2

(12) United States Patent
Villamil et al.

(10) Patent No.: US 12,589,251 B2
(45) Date of Patent: Mar. 31, 2026

(54) CONNECTOR FOR IMPLANTABLE MEDICAL DEVICE

(71) Applicant: Greatbatch Ltd., Clarence, NY (US)

(72) Inventors: Luis Daniel Villamil, Montevideo (UY); Ignacio Agustin Armesto, Montevideo (UY)

(73) Assignee: Greatbatch Ltd., Clarence, NY (US)

( * ) Notice: Subject to any disclaimer, the term of this patent is extended or adjusted under 35 U.S.C. 154(b) by 745 days.

(21) Appl. No.: 17/848,776

(22) Filed: Jun. 24, 2022

(65) Prior Publication Data

US 2022/0409910 A1 Dec. 29, 2022

Related U.S. Application Data

(60) Provisional application No. 63/215,255, filed on Jun. 25, 2021.

(51) Int. Cl.
*A61N 1/375* (2006.01)
*H01R 13/187* (2006.01)
*H01R 24/58* (2011.01)
*H01R 107/00* (2006.01)

(52) U.S. Cl.
CPC ......... *A61N 1/3754* (2013.01); *A61N 1/3752* (2013.01); *H01R 13/187* (2013.01); *H01R 24/58* (2013.01); *H01R 2107/00* (2013.01); *H01R 2201/12* (2013.01)

(58) Field of Classification Search
CPC ...... A61N 1/3754; A61N 1/05; A61N 1/3752; H01R 13/187; H01R 24/58; H01R 2107/00; H01R 2201/12; H01R 43/0221
See application file for complete search history.

(56) References Cited

U.S. PATENT DOCUMENTS

| | | | |
|---|---|---|---|
| 4,995,389 A | * | 2/1991 | Harris ...................... A61N 1/05 |
| | | | 607/37 |
| 7,047,077 B2 | | 5/2006 | Hansen et al. |
| 7,736,191 B1 | | 6/2010 | Sochor |
| 7,769,459 B2 | | 8/2010 | Balsells |
| 8,328,587 B2 | | 12/2012 | Dilmaghanian |
| 8,437,855 B2 | | 5/2013 | Sjostedt et al. |
| 8,690,609 B2 | | 4/2014 | Poon et al. |
| 9,466,915 B2 | | 10/2016 | Dilmaghanian |

(Continued)

OTHER PUBLICATIONS

Koch, et al., "Electrical connectors for neural implants: design, state of the art and future challenges of an underestimated component, Julia Koch et al., Journal of Neural Engineering", Oct. 29, 2019.

*Primary Examiner* — Tammie K Marlen
(74) *Attorney, Agent, or Firm* — Michael P. Horvath

(57) ABSTRACT

In various examples, a connector for an implantable medical device is configured to accept a lead therein and electrically couple to a lead contact of the lead. The connector includes a connector housing, which includes a bore portion including a bore hole therethrough. The bore hole includes a bore hole axis, the bore hole being sized and shaped to accept the lead within the bore hole. An attachment portion is coupled to the bore portion. The attachment portion includes an attachment hole within the attachment portion sized and shaped to accept a feedthrough wire within the attachment hole. The attachment hole includes an attachment hole axis offset from and non-parallel to the bore hole axis.

20 Claims, 9 Drawing Sheets

(56) References Cited

U.S. PATENT DOCUMENTS

| | | | |
|---|---|---|---|
| 9,943,695 | B2 | 4/2018 | Kast et al. |
| 9,950,180 | B2 | 4/2018 | Janzig et al. |
| 10,361,528 | B2 | 7/2019 | Dilmaghanian et al. |
| 10,520,001 | B2 | 12/2019 | Ghasiri |
| 10,639,484 | B2 | 5/2020 | Bilu et al. |
| 10,957,970 | B2 | 3/2021 | Li et al. |
| 11,005,305 | B2 | 5/2021 | Angara et al. |
| 2020/0016414 | A1 * | 1/2020 | Villamil ............... A61N 1/3752 |

* cited by examiner

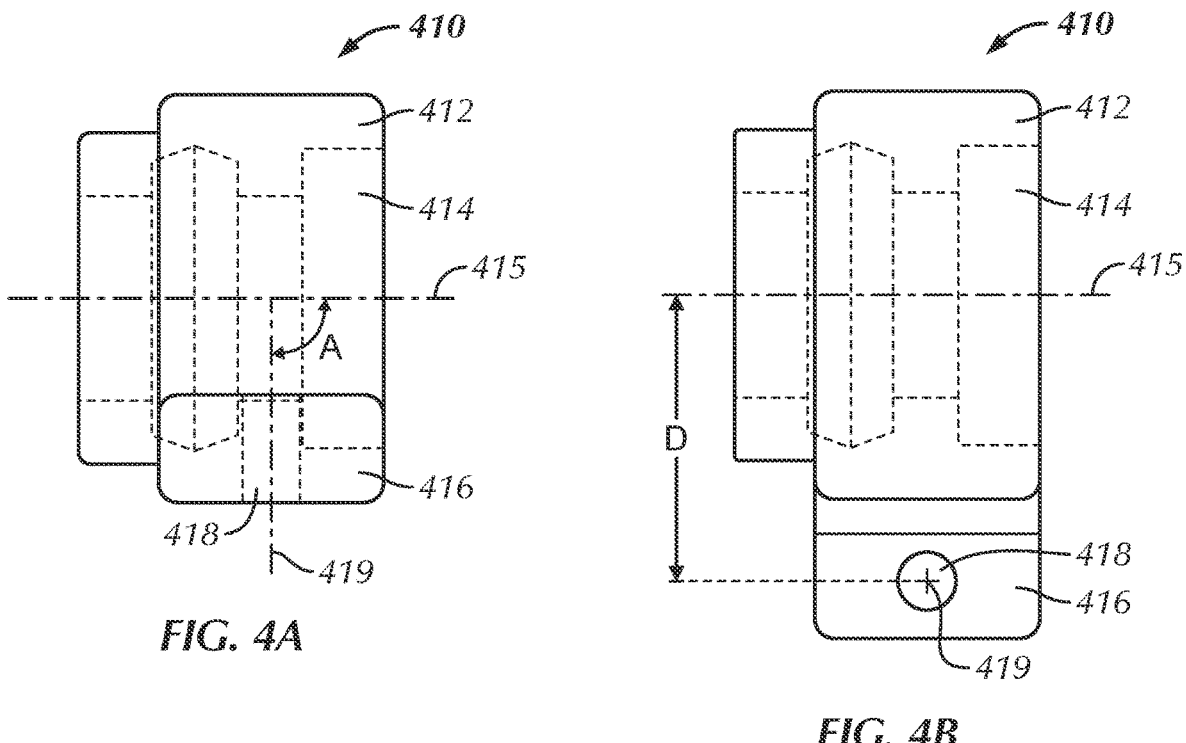
*FIG. 4A*
*FIG. 4B*
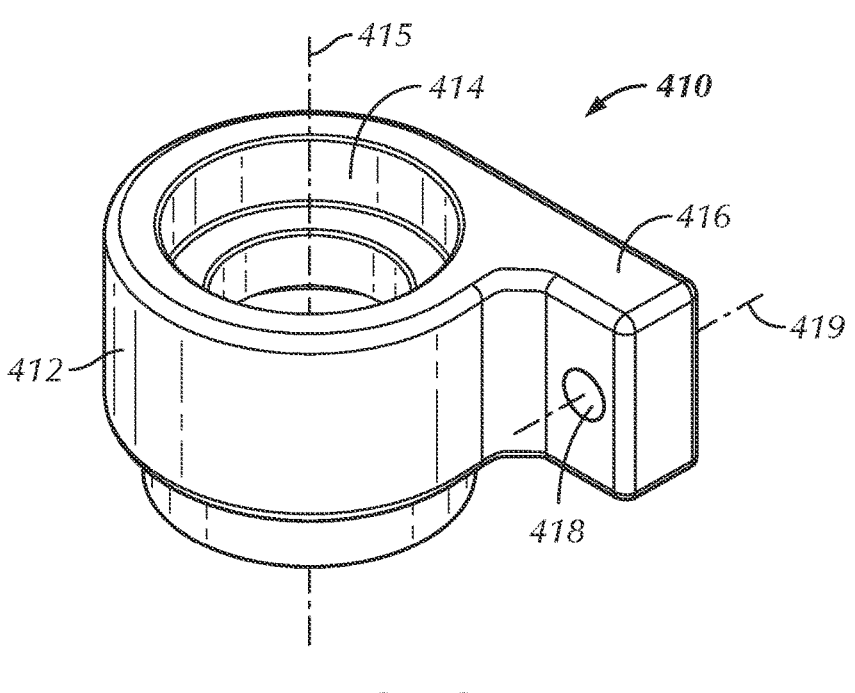
*FIG. 4C*

CONNECTOR FOR IMPLANTABLE MEDICAL DEVICE

CROSS REFERENCE TO RELATED APPLICATIONS

This application claims the benefit of priority to U.S. Provisional Application Ser. No. 63/215,255, filed on Jun. 25, 2021, entitled "SPRING CONNECTOR WITH LATERAL THROUGH HOLE," which is incorporated by reference herein in its entirety.

BACKGROUND

Referring to FIGS. 1A-3, a conventional implantable device connector 100 typically includes a substantially cylindrical metallic connector housing 110 with a spring 130 within a bore hole 112 through the connector housing 110 and a seal 120. The connector 100 includes a connector axis 101. The bore hole 112 is typically sized and shaped to receive a lead therein and is disposed along a bore hole axis 111 of the connector housing 110. Usually, the connector housing 110 is cylindrical to allow for resistance welding of the connector housing 110 to a feedthrough wire 180. Typically, the feedthrough wire 180 is resistance welded to an exterior surface of the connector housing 110. The connector 100 typically includes the seal 120 adjacent to the connector housing 110 in order to seal against the lead to inhibit ingress of fluids or other contaminants within the bore hole 112 of the connector housing 110.

Referring to FIG. 3, typical positioning of the feedthrough wires 180 and the connectors 100 is shown. Two or more connectors 100 can be coupled together in series to form a stack assembly 150, with each connector 100 of the stack assembly 150 corresponding to a feedthrough wire 180. The axes 101 of the connectors 100 of the stack assembly 150 are all substantially aligned along a stack axis 151 to allow for insertion of a lead or other medical device within the stack assembly 150.

When each connector 100 is coupled to one of the corresponding feedthrough wires 180, typical systems only allow welding of the feedthrough wires 180 in a direction X substantially perpendicular to the feedthrough wires 180, which requires increased free space within a device header. As such, typical connector housings 110 do not allow for axial laser welding between the feedthrough wire 180 and the connector housing 110 without using any fixture, jig, tooling, or the like to secure the contact between the feedthrough wire 180 and the connector housing 110. This requires extra space in the device header which requires a higher volume of the device.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the present subject matter can be used to allow connectors within an implantable medical device to be closer to the hermetic electronic enclosure of the device, thereby potentially reducing the wire routing operations within a header of the device and reducing the free space needed in the header to allow for the welding of feedthrough wires to the connectors. Also, the present subject matter is advantageous in that it is conducive to automatization of processes for the attachment of the connectors to the feedthrough wires, at least in part due to the enhanced welding junctions. In various examples, the present subject matter is advantageous in that it provides a more reliable and simpler-to-manufacture design for the header of the device. To better illustrate the devices described herein, a non-limiting list of examples is provided here:

Example 1 can include subject matter that can include a connector for an implantable medical device. The connector is configured to accept a lead therein and electrically couple to a lead contact of the lead. The implantable medical device includes a feedthrough wire. A connector housing includes a bore portion including a bore hole therethrough. The bore hole includes a bore hole axis. The bore hole is sized and shaped to accept the lead within the bore hole. An attachment portion is coupled to the bore portion. The attachment portion includes an attachment hole within the attachment portion sized and shaped to accept the feedthrough wire within the attachment hole. The attachment hole includes an attachment hole axis offset from and non-parallel to the bore hole axis.

In Example 2, the subject matter of Example 1 is optionally configured such that the bore portion is substantially cylindrical.

In Example 3, the subject matter of Example 1 or 2 optionally includes a spring disposed within the bore hole of the bore portion. The spring is configured to electrically couple to the lead contact with the lead disposed within the bore hole.

In Example 4, the subject matter of any one of Examples 1-3 is optionally configured such that the attachment portion extends outwardly from the bore portion.

In Example 5, the subject matter of any one of Examples 1-4 is optionally configured such that the bore hole axis is substantially perpendicular to the attachment hole axis.

In Example 6, the subject matter of any one of Examples 1-5 optionally includes a seal coupled to the bore portion. The seal is configured to sealingly engage with the lead with the lead disposed within the bore hole.

Example 7 can include, or can optionally be combined with any one of Examples 1-6 to include subject matter that can include a stack assembly for an implantable medical device. The stack assembly is configured to accept a lead therein and electrically couple to at least two lead contacts of the lead. The implantable medical device includes at least two feedthrough wires. The stack assembly includes at least two connector housings including a first connector housing and a second connector housing. Each of the connector housings includes a bore portion including a bore hole therethrough. The bore hole includes a bore hole axis. The bore hole is sized and shaped to accept the lead within the bore hole. An attachment portion is coupled to the bore portion. The attachment portion includes an attachment hole within the attachment portion sized and shaped to accept one of the feedthrough wires within the attachment hole. The attachment hole includes an attachment hole axis offset from and non-parallel to the bore hole axis, wherein the bore hole axes of the at least two connector housings are colinear. At least one seal is disposed between the first connector housing and the second connector housing. The seal is configured to sealingly engage with the lead with the lead disposed within the bore holes of the first connector housing and the second connector housing.

In Example 8, the subject matter of Example 7 is optionally configured such that the bore portion of each of the first connector housing and the second connector housing is substantially cylindrical.

In Example 9, the subject matter of Example 7 or 8 optionally includes at least two springs with one spring disposed within the bore hole of the bore portion of each of the first connector housing and the second connector housing. Each of the springs is configured to electrically couple to one of the lead contacts with the lead disposed within each of the bore holes.

In Example 10, the subject matter of any one of Examples 7-9 is optionally configured such that the attachment portion of each of the connector housings extends outwardly from the bore portion.

In Example 11, the subject matter of any one of Examples 7-10 is optionally configured such that the bore hole axis of each of the connector housings is substantially perpendicular to the attachment hole axis.

In Example 12, the subject matter of any one of Examples 7-11 is optionally configured such that the bore holes of the at least two connector housings form a bore within the stack assembly. The bore is sized and shaped to accept a portion of the lead within the bore.

In Example 13, the subject matter of Example 12 optionally includes at least two springs with one spring disposed within the bore hole of the bore portion of each of the first connector housing and the second connector housing. Each of the springs is configured to electrically couple to one of the lead contacts with the lead disposed within the bore hole.

In Example 14, the subject matter of Example 13 is optionally configured such that one of the at least two springs is disposed circumferentially around the bore hole of each of the at least two connector housings. Each of the at least two springs is configured to abut and electrically couple to a different one of the at least two lead contacts with the portion of the lead disposed within the bore of the stack assembly.

Example 15 can include, or can optionally be combined with any one of Examples 1-14 to include subject matter that can include a stack assembly for an implantable medical device. The stack assembly is configured to accept a lead therein and electrically couple to a plurality of lead contacts of the lead. The implantable medical device includes a plurality of feedthrough wires. The stack assembly includes a plurality of connector housings corresponding to the plurality of lead contacts of the lead. Each of the plurality of connector housings includes a bore portion including a bore hole therethrough. The bore hole includes a bore hole axis. The bore hole is sized and shaped to accept the lead within the bore hole. An attachment portion is coupled to the bore portion. The attachment portion includes an attachment hole within the attachment portion sized and shaped to accept one of the plurality of feedthrough wires within the attachment hole. The attachment hole includes an attachment hole axis offset from and non-parallel to the bore hole axis, wherein the bore hole axes of the plurality of connector housings are colinear. The stack assembly includes a plurality of seals with one seal of the plurality of seals disposed between each pair of adjacent connector housings of the plurality of connector housings. Each of the plurality of seals is configured to sealingly engage with the lead with the lead disposed within the bore holes of the plurality of connector housings. The stack assembly includes a plurality of springs with one spring disposed within the bore hole of the bore portion of each of the plurality of connector housings. Each of the springs is configured to electrically couple to one of the plurality of lead contacts with the lead disposed within each of the bore holes, wherein the bore holes of the plurality of connector housings form a bore within the stack assembly. The bore is sized and shaped to accept a portion of the lead within the bore.

In Example 16, the subject matter of Example 15 is optionally configured such that the bore portion of each of the first connector housing and the second connector housing is substantially cylindrical.

In Example 17, the subject matter of Example 15 or 16 is optionally configured such that the attachment portion of each of the connector housings extends outwardly from the bore portion.

In Example 18, the subject matter of any one of Examples 15-17 is optionally configured such that the bore hole axis of each of the connector housings is substantially perpendicular to the attachment hole axis.

In Example 19, the subject matter of any one of Examples 15-18 is optionally configured such that one of the plurality of springs is disposed circumferentially around the bore hole of each of the plurality of connector housings. Each of the plurality of springs is configured to abut and electrically couple to a different one of the plurality of lead contacts with the portion of the lead disposed within the bore of the stack assembly.

In Example 20, the subject matter of any one of Examples 15-19 is optionally configured such that each seal of the plurality of seals is substantially ring-shaped and formed of a resilient material to seal around the lead disposed within the bore of the stack assembly.

BRIEF DESCRIPTION OF THE DRAWINGS

FIGS. 4A-4C are views of a connector housing for an implantable medical device, the connector housing being in accordance with at least one example of the invention.

DETAILED DESCRIPTION

Figure 1A:
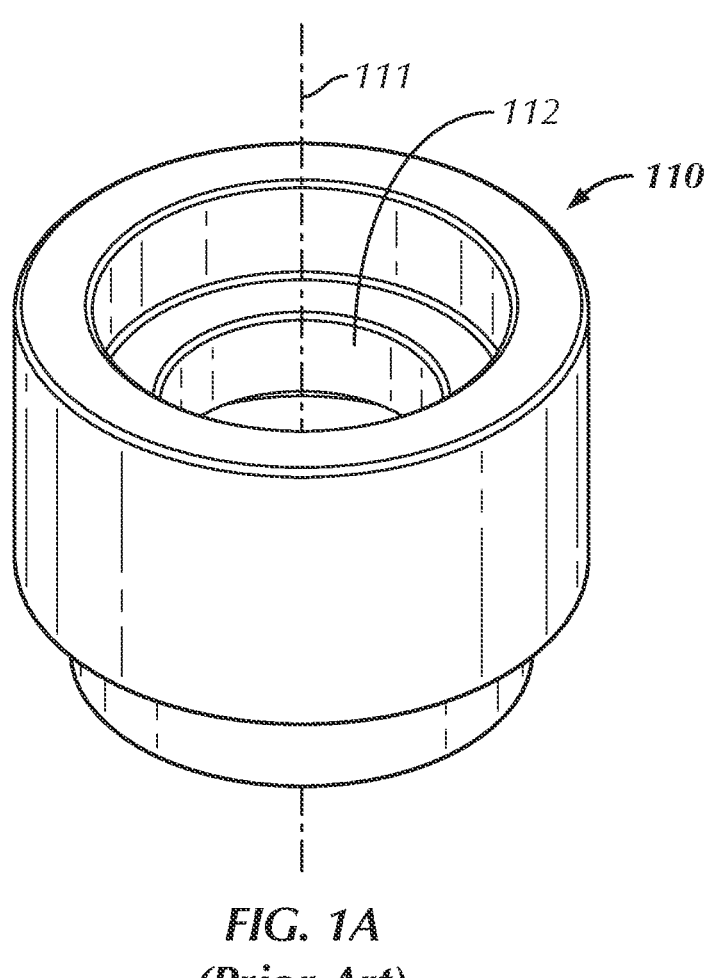
FIGS. 1A and 1B are views of a conventional connector housing for an implantable medical device.
Figure 1B:
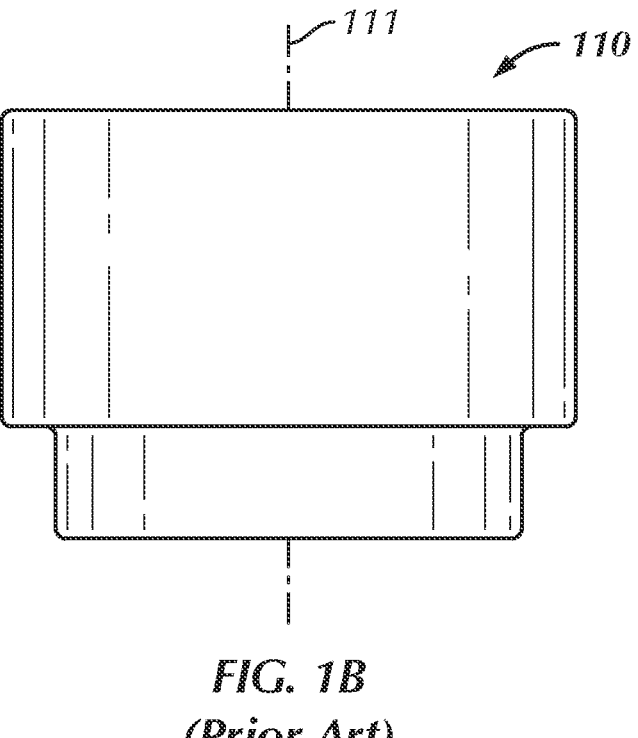
Figure 2A:
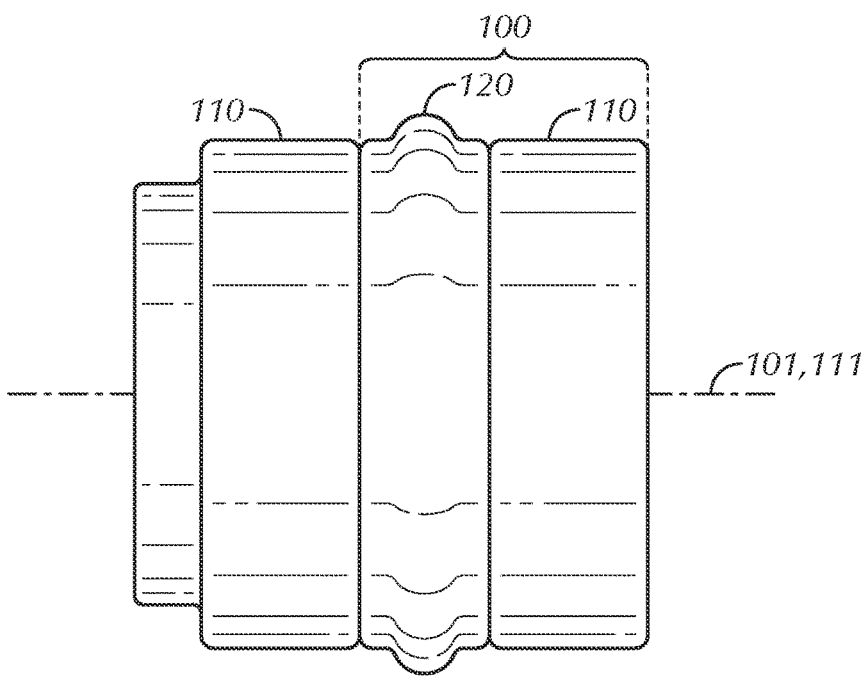
FIGS. 2A and 2B are views of conventional connectors for an implantable medical device.
Figure 2B:
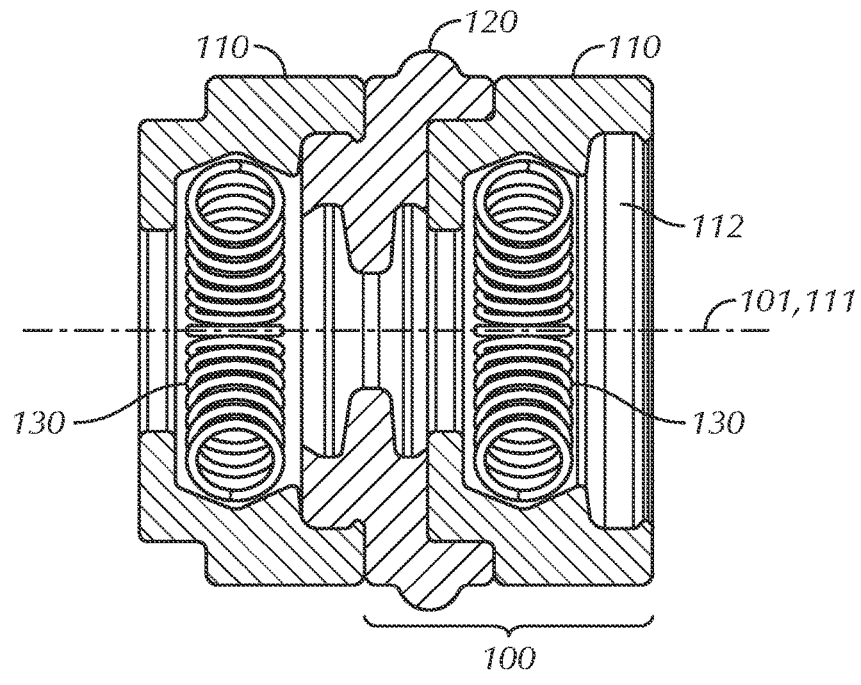

The present invention relates generally to a connector for an implantable medical device. More specifically, the present invention relates to one of more connectors that form one or more stack assemblies for use within a header of an implantable medical device to electrically couple one or more leads to the device. Although the description herein relates to a connector and/or a stack assembly for an implantable medical device, the present subject matter is not intended to be so limited. As such, it is contemplated herein that the present subject matter can be used with various other medical devices and/or components.

In some examples, the present subject matter allows for a higher density of electrical contacts between the stimulation/ sensing leads and the device in the device header. Current conventional systems are large and bulky for large channel count lead or headers (for instance, headers with more than eight contacts) given that there is space required for routing wires from the hermetic electronic enclosure to the lead contact rings. The present inventive subject matter, in some examples, allows the connectors to be closer to the hermetic electronic enclosure, thereby potentially reducing the wire routing operations within the header and reducing the free space needed in the header to allow for the welding of the feedthrough wires to the connectors. Moreover, in some examples, the present inventive subject matter is conducive to automatization processes, at least in part due to the enhanced welding junctions.

The purpose of the present inventive subject matter is to reduce the size of an implantable device (for instance, an implantable stimulation and/or sensing device) by modifying a welding section of a connector to include a welding feature for a more reliable and simpler-to-manufacture design for the header of the device.

There are many benefits to the present inventive subject matter, including, but not limited to: allowing for a smaller device with high channel counts (for instance, more than eight contacts); allowing for low profile headers, which greatly reduces the device volume, and, therefore, the implant is less invasive to the human patient; improving the welding joint between the wires and the connectors for laser welding; allowing for laser welding with reduced routing of the wires; allowing for laser welding without any routing of the wires; and allowing for a device assembly process to be automatized with high reliability welding and decreased assembly manipulation time.

The present inventive subject matter provides a connector housing to allow the insertion of a feedthrough wire through a portion of the connector housing, which, in turn, allows for laser welding of the feedthrough wires to the connector housings in a direction substantially axial to the feedthrough wires. The present inventive subject matter also furnishes a constraint of the wire by design, and, therefore, the welding junction is unchanged within units, thereby, at least in part, increasing reliability of the device.

As described above, conventional systems only allow welding of the feedthrough wires in a direction perpendicular to the feedthrough wires, which requires increased free space within the device header. Since the present inventive subject matter allows for the axial welding of the feedthrough wires, the lead cavities or stacks can be placed closer to each other, thereby reducing the header volume to enable a low-profile header.

Conventional connector housings do not allow for axial laser welding between the wire and the connector without using any fixture/jig/tooling to secure the contact between the parts. This requires extra space in the header which requires a higher volume of the device. The present inventive subject matter does not require any fixture/jig/tooling since the wire can be welded once inserted in the connector housing. Also, the weld joint of the present inventive subject matter is more suited for laser welding than the weld joint of the above-described conventional solutions.

Referring to FIGS. 4A-9, in some examples, an implantable medical device 470 is configured to be at least partially insertable within a patient. In some examples, the implantable medical device 470 can include various implantable medical devices, such as, but not limited to, a pacemaker, a defibrillator, a neurostimulator, a cochlear implant, a pump, and/or a monitor, to name a few. In various examples, the implantable medical device 470 includes a lead 490 or other elongate device electrically and physically coupled to the implantable medical device 470. As stated above, it is advantageous to make such implantable medical devices smaller and smaller to facilitate placement of the implantable medical device within the patient, reduce complications and recovery time for the patient, and allow for increased numbers of channels. To do so, in some examples, the present inventive subject matter seeks to reduce the size of a header 474 of the implantable medical device 470. In some examples, the present inventive subject matter includes a connector 400 for use within the header 474 to, among other things, reduce space needed within the header 474 to accommodate the connector 400 and improve the quality of a connection between the connector 400 and a feedthrough wire 480 of the implantable medical device 470.

Referring now to FIGS. 4A-5B, in some examples, the connector 400 is configured to accept the lead 490 (FIG. 9) therein and electrically couple to a lead contact 494 (FIG. 9) of the lead 490. In some examples, the connector 400 includes a connector housing 410. In some examples, the connector housing 410 is formed from a conductive material and is formed into a low-profile shape capable of electrically coupling with the lead 490. In some examples, the connector housing 410 includes a bore portion 412 including a bore hole 414 therethrough. In some examples, the bore hole 414 includes a bore hole axis 415. The bore hole 414, in some examples, is sized and shaped to accept the lead 490 within the bore hole 414. In some examples, the bore hole 414 is substantially circular in cross section and extends through the bore portion 412 of the connector housing 410 along the bore hole axis 415. In some examples, the connector housing 410 is substantially cylindrical in shape, such that the overall shape of the connector housing 410 is generally cylindrical in shape, although it can include various steps, indentations, facets, or other features. In other examples, the connector housing 410 can include shapes other than substantially cylindrical, should other geometries be more desirable in other devices.

In some examples, the connector housing 410 includes an attachment portion 416 coupled to the bore portion 412. The attachment portion 416, in some examples, extends outwardly from the bore portion 412. In further examples, the attachment portion 416 extends outwardly from the bore portion 412 in a direction away from the bore hole axis 415. In some examples, the attachment portion 416 includes an attachment hole 418 within the attachment portion 416, wherein the attachment hole 418 is sized and shaped to accept the feedthrough wire 480 within the attachment hole 418. The attachment hole 418, in some examples, includes an attachment hole axis 419 offset from and non-parallel to the bore hole axis 415. In some examples, the attachment hole axis 419 is spaced from the bore hole axis 415 by a distance D. In some examples, the attachment hole axis 419 is substantially perpendicular to the bore hole axis 415. The term "substantially perpendicular" is used herein to mean that the attachment hole axis 419 does not have to be exactly at ninety degrees to the bore hole axis 415 but can be within a few degrees of being perpendicular to be considered "substantially perpendicular."

In other examples, the attachment hole axis 419 can be at angles other than perpendicular to the bore hole axis 415, such as at an acute angle, an obtuse angle, or the like. In still other examples, the attachment hole axis 419 is parallel to the bore hole axis 415. In some examples, the attachment hole 418 is disposed with respect to the connector housing 410 in such a way as to be readily accessible in order to join the feedthrough wire 480 disposed within the attachment hole 418 to the connector housing 410. In some examples, the bore portion 412 includes a substantially cylindrical shape with the attachment portion 416 extending substantially tangentially from the bore portion 412. In this way, the attachment portion 416 allows for the attachment hole axis 419 to be spaced from the bore hole axis 415 by the distance D, thereby making the attachment hole 418 easily accessible to facilitate placement of the feedthrough wire 480 within the attachment hole 418 and attachment of the connector housing 410 to the feedthrough wire 480.

Figure 3:
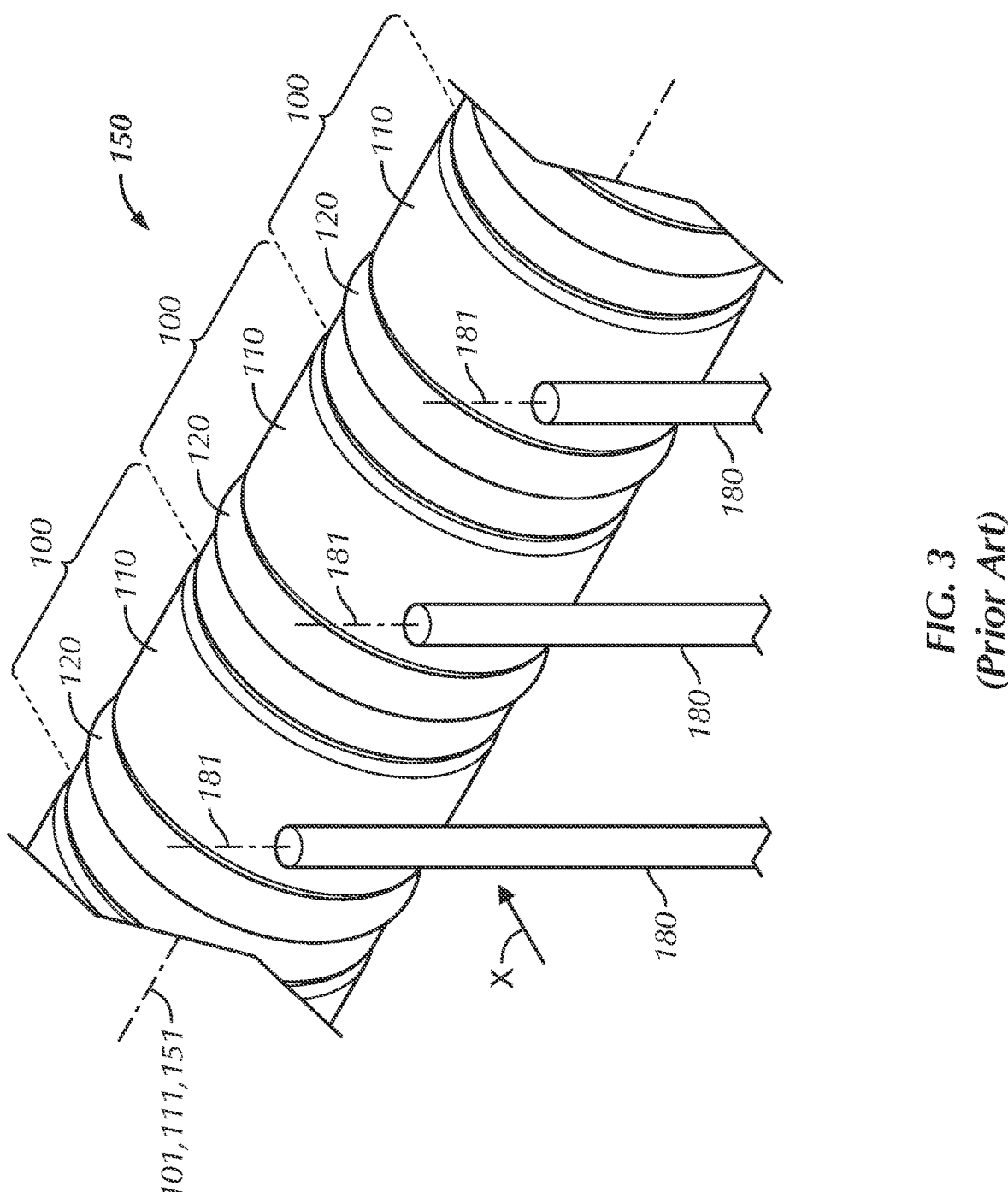
FIG. 3 is a perspective view of a portion of a conventional stack assembly aligned with feedthrough wires of an implantable medical device.
Figure 5A:
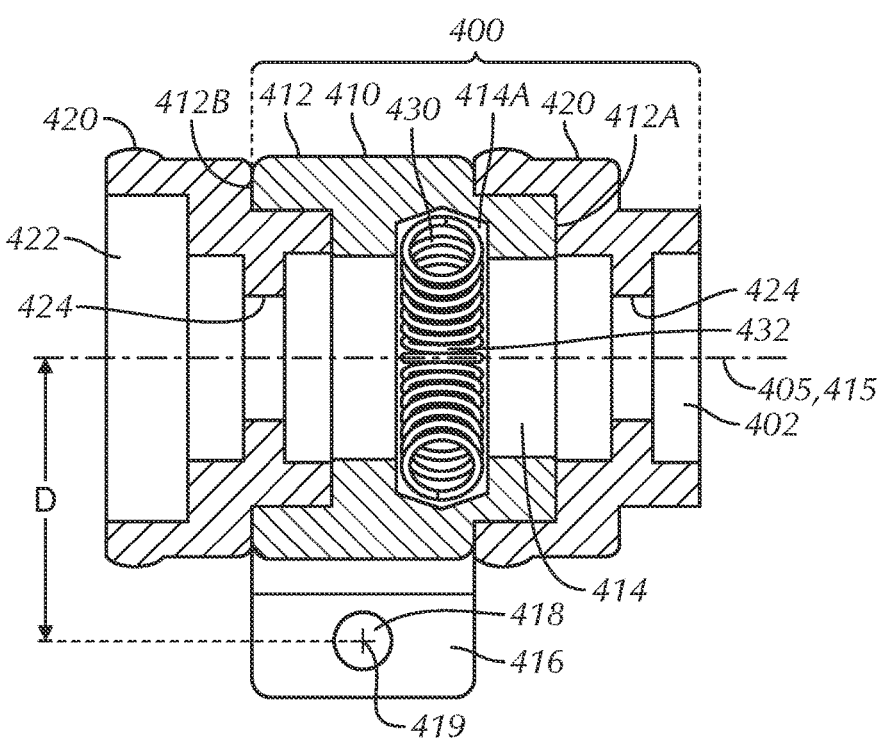
FIGS. 5A and 5B are views of a connector for an implantable medical device, the connector being in accordance with at least one example of the invention.
Figure 5B:
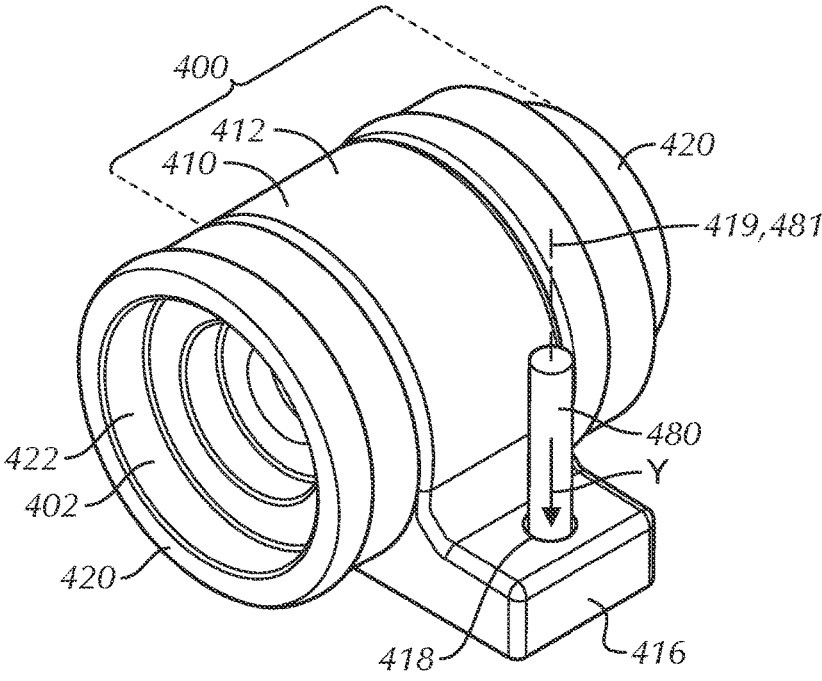

In some examples, the attachment hole 418 being offset from and non-parallel to the bore axis 415 allows for relatively easy access to an interface of the feedthrough wire 480 and the attachment portion 416 and allows for substantially axial welding along direction Y of the feedthrough wire 480 to the attachment portion 416. Moreover, in some examples, with the feedthrough wire 480 being disposed within the attachment hole 418, it provides a more solid interface between the feedthrough wire 480 and the attachment portion 416 of the connector housing 410 than is possible with conventional connector systems (such as that which is shown in FIG. 3) where the feedthrough wire simply abuts an exterior (and often rounded) surface of the connector. Additionally, in some examples, substantially axial welding in the direction Y allows for a more reliable junction between the feedthrough wire 480 and the attachment portion 416 of the connector housing 410 than is achieved with conventional connector systems in which the feedthrough wire is welded in a direction substantially perpendicular to the feedthrough wire. Such a configuration also allows for the connector housings 410 to be placed closer together within a device because less space is needed in between connector housings 410 to axially weld the feedthrough wires 480 than is needed to perpendicularly weld feedthrough wires to conventional connector housings.

In some examples, the connector housing 410 makes up just a portion of the connector 400. In addition to the connector housing 410, in some examples, the connector 400 further includes a spring 430 disposed within the bore hole 414 of the bore portion 412. In some examples, the spring 430 is configured to electrically couple to the lead contact 494 (FIG. 9) with the lead 490 disposed within the bore hole 414. In some examples, the spring 430 is generally ring-shaped or generally donut-shaped with a spring hole 432 that is sized to abut an outside surface of the lead contact 494 with the lead 490 disposed through the spring 430 in order to provide for electrical coupling of the spring 430 with the lead contact 494. In some examples, the spring 430 is sized such that a diameter of the spring hole 432 is at least slightly smaller than an outer diameter of the lead contact 494 to ensure contact of the spring 430 with the lead contact 494.

In some examples, the spring 430 is sized to fit within a spring cavity 414A within the bore 414 of the connector housing 410. In further examples, the spring 430 is sized such that the spring 430 is at least slightly compressed when disposed within the spring cavity 414A so as to exert at least a slight outward force within the spring cavity 414A of the connector housing 410, thereby ensuring contact with the connector housing 410 and inhibiting the spring 430 from falling out of the connector housing 410.

In this way, in some examples, the spring 430 allows for the connector housing 410 to be electrically coupled to the lead contact 494 of the lead 490 with the lead 490 disposed within the bore 414 of the connector housing 410, which, in turn, electrically couples the lead contact 494 to the feedthrough wire 480.

In some examples, the connector 400 includes at least one seal 420. In some examples, the seal 420 is coupled to the bore portion 412 of the connector housing 410. In some examples, the seal 420 is generally ring-shaped with a seal opening 422 through the seal 420 sized to accept the lead 490 within the seal opening 422. In some examples, the seal 420 is configured to sealingly engage with the lead 490 with the lead 490 disposed within the seal opening 422. With the seal 420 attached to the connector housing 410, in some examples, the seal 420 acts to inhibit foreign materials and/or fluid from entering the bore hole 414 of the connector housing 410 with the lead 490 disposed within the seal opening 422 and the bore hole 414. In some examples, the seal 420 acts to electrically isolate one connector housing 410 from another housing 410 and/or one lead contact 494 from another lead contact 494. The seal 420, in some examples, includes a silicone ring configured to be electrically insulative and resilient in order to provide for sealing engagement with the lead 490 within the seal opening 422. In other examples, other materials can be used to form the seal 420 provided that the materials are electrically insulative and resilient.

In some examples, the seal 420 includes a reduced diameter portion 424 that extends inwardly within the seal opening 422 and includes a diameter that is sized to abut the outside surface of the lead 490 in order to provide for sealing engagement of reduced diameter portion 424 of the seal 420 with the lead 490. In some examples, the reduced diameter portion of the seal 420 is sized such that the diameter of the reduced diameter portion 424 is at least slightly smaller than the outer diameter of the lead 490 to ensure sealing engagement of the seal 420 with the lead 490.

In some examples, the seal 420 is disposed at a first side 412A of the bore portion 412 of the connector housing 410. In some examples, the seal 420 is disposed at a second side 412B of the bore portion 412 of the connector housing 410. In still other examples, one seal 420 is disposed at the first side 412A of the bore portion 412 of the connector housing 410, and one seal 420 is disposed at the second side 412B of the bore portion 412 of the connector housing 410. In some examples, the seal 420 is frictionally engaged with the first side 412A and/or the second side 412B of the bore portion 412 of the connector housing 410. In other examples, the seal 420 can be affixed to the bore portion 412 using an adhesive in addition to or instead of the frictional engagement of the seal 420 to the bore portion 412.

In some examples, the connector 400 includes the connector housing 410, the seal 420, and the spring 430. When assembled, in some examples, the connector 400 includes a connector bore 402. In some examples, the connector bore 402 is made up by the bore hole 414 of the connector housing 410, the seal opening 422 of the seal, and the spring hole 432 of the spring 430. In some examples, the bore hole 414, the seal opening 422, and the spring hole 432 are aligned along a connector bore axis 405 to form the bore hole 402. The connector bore axis 405, in some examples, extends along the bore hole axis 415 of the connector housing 410.

Figure 6:
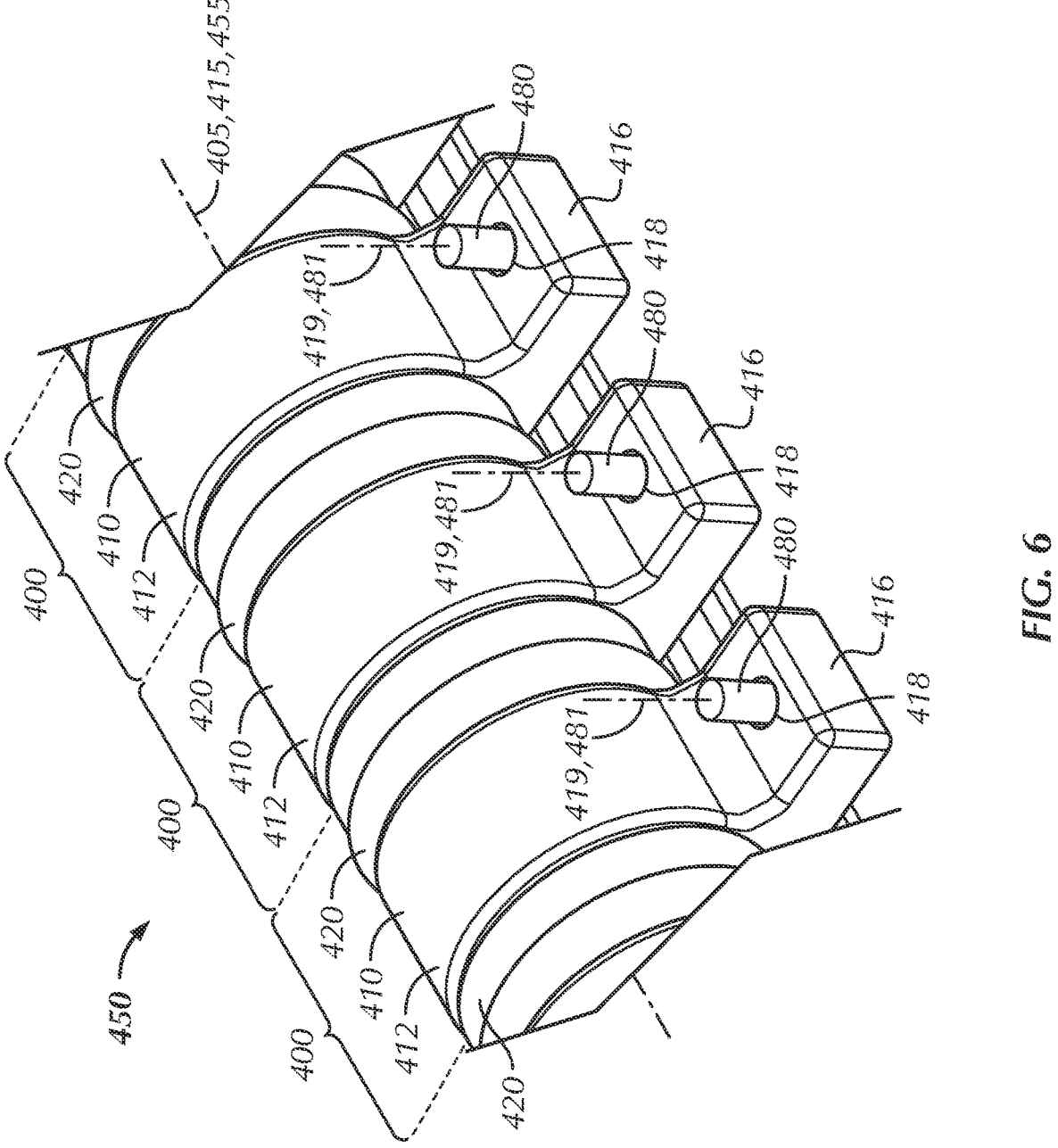
FIG. 6 is a perspective view of a portion of a stack assembly aligned with feedthrough wires of an implantable medical device, the stack assembly being in accordance with at least one example of the invention.

Referring now to FIG. 6, in some examples, two or more connectors 400, as described above, are coupled together to form a stack assembly 450. In some examples, the connector housings 410 of the at least two connectors 400 of the stack assembly 450 are coupled together with the seal 420 in between adjacent connector housings 410. In some examples, the number of connectors 400 in the stack assembly 450 corresponds to the number of lead contacts 494 of the lead 490 (see FIG. 9). In some examples, the connectors 400 are coupled together such that the connector bore axes 405 (and/or the bore hole axes 415) are colinear to form a bore axis 455 of the stack assembly 450. The connectors 400 of the stack assembly 450, in some examples, are configured and/or arranged such that the attachment portions 416 and, more specifically, the attachment holes 418 are able to accept the corresponding feedthrough wires 418 therein in order to allow for electrical connection of each of the connectors 400 with each of the feedthrough wires 418 of the implantable medical device 470 (FIG. 9).

Figure 7:
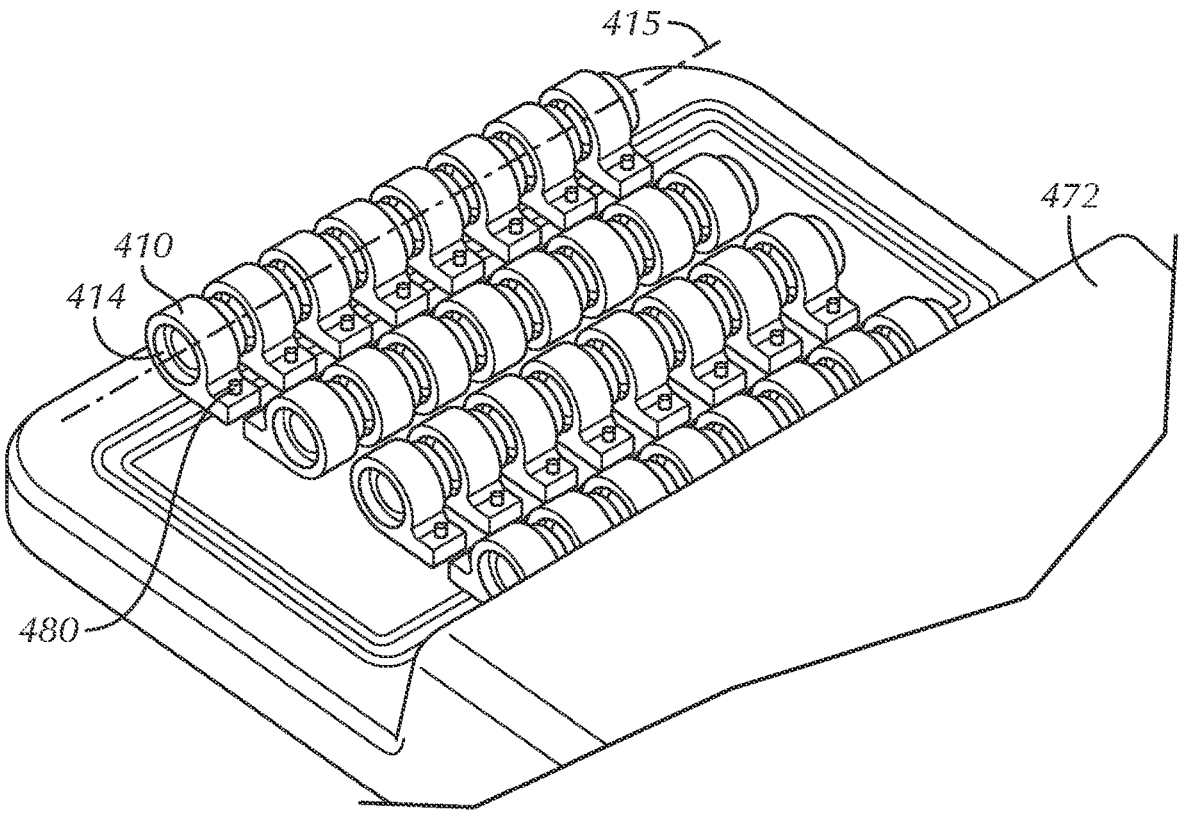
FIG. 7 is a perspective view of a header of an implantable medical device showing an exemplary alignment of connector housings within the header, the connector housing being in accordance with at least one example of the invention.
Figure 8:
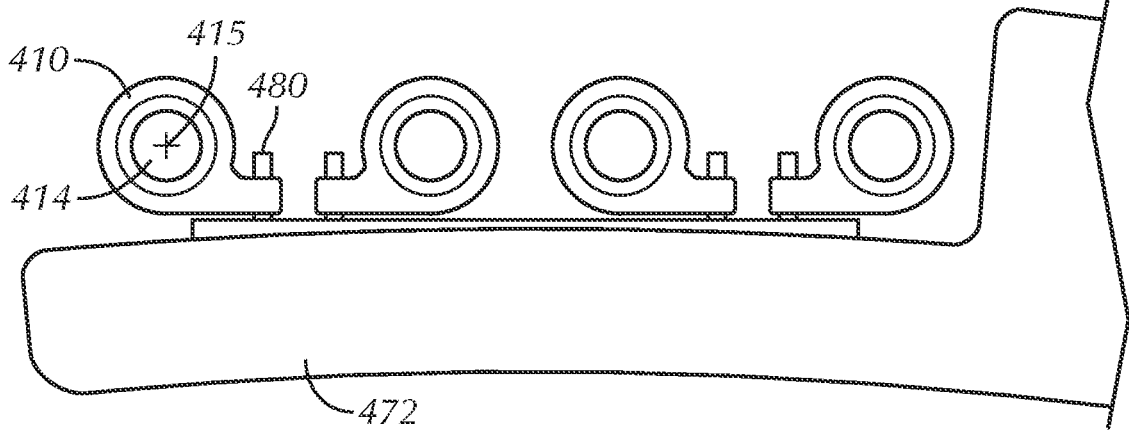
FIG. 8 is a side view of a header of an implantable medical device showing an exemplary alignment of connector housings within the header, the connector housing being in accordance with at least one example of the invention.
Figure 9:
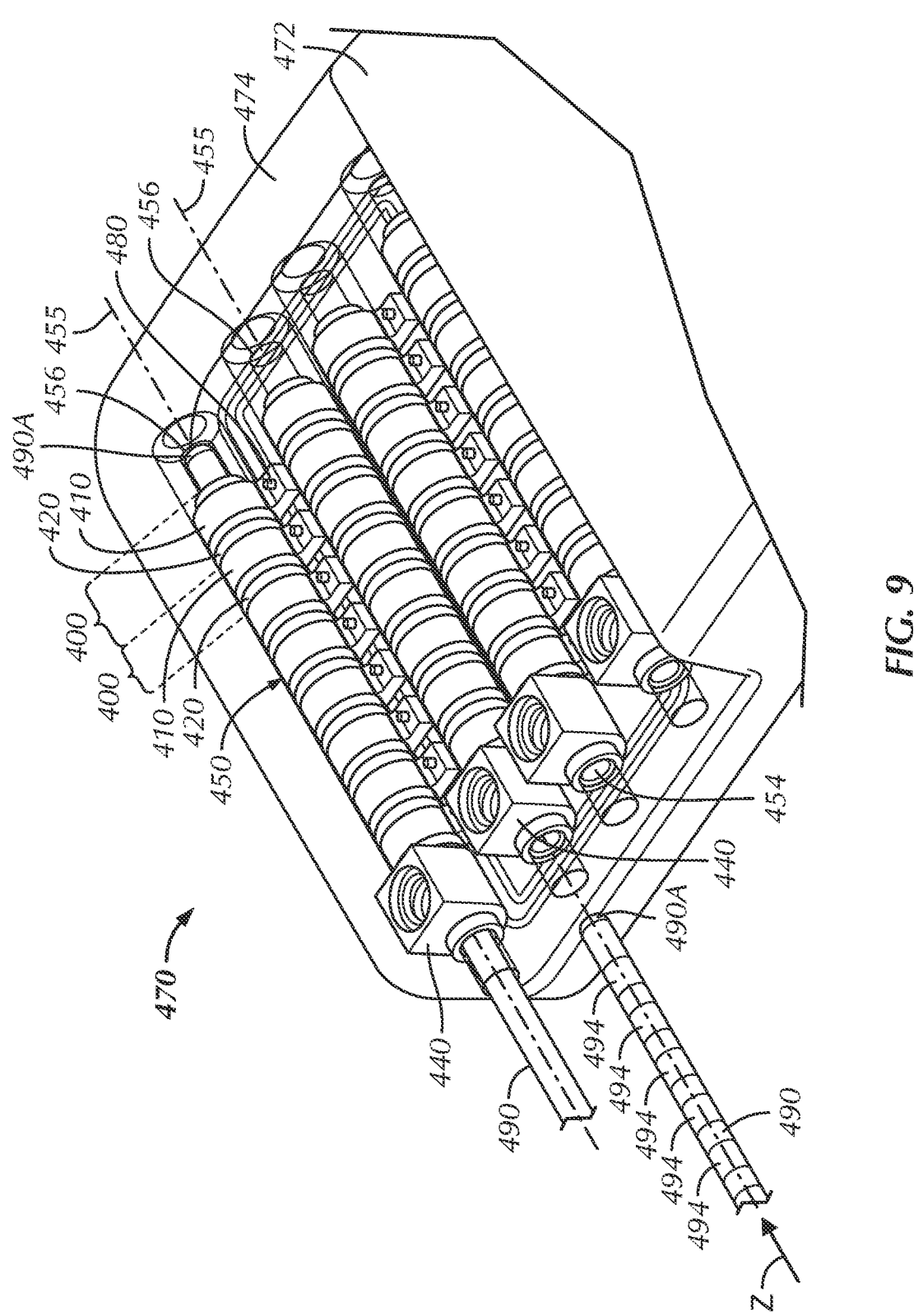
FIG. 9 is a perspective view of a header of an implantable medical device showing stack assemblies within the header, the stack assemblies being in accordance with at least one example of the invention.

Referring now to FIGS. 7 and 8, in some examples, the connector housings 410 are arranged in different rows for forming stack assemblies to form implantable lead cavity ports in order to electrically connect the implantable medical device 470 to the one or more leads 490 (FIG. 9). In the example shown, four rows of eight connector housings 410 are arranged within the header of the implantable medical device in order to accommodate four eight-electrode leads. Although this design is shown, it should be apparent that the inventive subject matter described herein can be used to form more or less than four stack assemblies, each with more or less than eight connector housings 410 in order to accommodate more or fewer than four leads with varying electrode configurations, depending upon the application of the implantable medical device. In some examples, the bore hole axes 415 of the connector housings 410 of each row of connector housings 410 are colinear with one another so that the bore holes 414 are all aligned with one another. Moreover, in some examples, the connector housings 410 are arranged to allow for easy access to the feedthrough wires 480 to facilitate welding of the feedthrough wires 480 extending from a housing 472 of the implantable medical device to the connector housings 410.

Referring now to FIG. 9 (with continued reference to FIGS. 4A-6), an example of the implantable medical device 470 incorporating the connectors 400, as described herein, includes four stack assemblies 450 within a header 474 of the implantable medical device 470. In some examples, each stack assembly includes eight connectors 400 arranged within the header 474 of the implantable medical device 470 in order to accommodate four eight-electrode leads 490. Although this design is shown, it should be apparent that the inventive subject matter described herein can be used to form more or less than four stack assemblies 450, each with more or less than eight connectors 400 in order to accommodate more or fewer than four leads 490 with varying electrode configurations, depending upon the application of the implantable medical device 470. As described above, in some examples, the stack assembly 450 includes two or more connectors 400 coupled together in a line, such that the connector bore axes 405 of the two or more connectors 400 are colinear. In this way, in some examples, the connector bores 402 of the two or more connectors 400 are aligned to form a bore 454 of the stack assembly 450. In some examples, the bore 454 of the stack assembly 450 includes a bore axis 455. In further examples, the bore axis 455 is colinear with the connector bore axes 405.

In some examples, the implantable medical device 470 includes the housing 472, within which are various electronic modules, depending upon the application for the implantable medical device 470; a power source; potentially a capacitor, again depending upon the application for the implantable medical device 470; and/or other internal components. Electrically coupled to one or more of the internal components are the feedthrough wires 480 that, in some examples, are hermetically sealed with and extend from the housing 472 and into the header 474. Within the header 474, in some examples, at least one connector 400 is electrically coupled to the feedthrough wire 480, for instance, by axially welding the feedthrough wire 480 within the attachment hole 418 of the attachment portion 416 of the connector housing 410. In further examples, two or more connectors 400 are arranged, as described herein, to form one or more stack assemblies 450, with connection points between the feedthrough wires 480 and the attachment holes 418 of the attachment portions 416 of the connector housings 410 being easily accessible for substantially axial welding thereof. In the example of FIG. 9, the positioning of the connection points between the feedthrough wires 480 and the attachment holes 418 of the attachment portions 416 of the connector housings 410 are accessible from above (with respect to the view shown in FIG. 9) for welding without the need for special jigs or other tooling and with the connectors 400 being relatively closely spaced to one another. As compared to the present examples of the inventive subject matter described herein, a similar number of conventional connectors in a conventional header would require increased space between connectors and/or specialized tooling in order to perform substantially perpendicular welding of the feedthrough wires to the sides of the connector housings. In this way, the header 474 of the present examples of the inventive subject matter can be smaller and/or lower profile than a conventional header.

In some examples, each of the stack assemblies 450 can include a screw connector 440 to accept a set screw therein in order to mechanically secure the lead 490 inside the bore 454. In some examples, the stack assembly 450 includes the seals 420 disposed between adjacent connector housings 410 and at the end of the stack assembly 450 for proper sealing and electrical insulation of the connector housings 410. In still other examples, the stack assembly can include an end cap 456 to control a position of a proximal end 490A of the lead 490.

In some examples, the stack assembly 450 is configured to accept the lead 490 therein and electrically couple to two or more lead contacts 494 of the lead 490. In some examples, the implantable medical device 470 includes two or more feedthrough wires 480. The stack assembly 450, in some examples, includes at least two connector housings 410, as described herein, including a first connector housing 410 and a second connector housing 410, with at least one seal 420 disposed between the first connector housing 410 and the second connector housing 410. The seal 420, in some examples, is configured to sealingly engage with the lead 490, as described herein, with the lead 490 disposed within the bore holes 414 of the first connector housing 410 and the second connector housing 410. In some examples, the two or more connector housings 410 each include the bore portion 412 with the bore hole 414 being sized and shaped to accept the lead 490 within the bore hole 414 and the attachment portion 416 coupled to the bore portion 412. In some examples, the bore hole axes 415 of the connector housings 410 of the stack assembly 450 are colinear. The bore holes 414 of the connector housings 410 of the stack assembly 450, in some examples, form the bore 454 within the stack assembly 450. In some examples, the bore 454 is sized and shaped to accept a portion of the lead 490 within the bore 454. In this way, in some examples, the proximal end 490A of the lead 490 can be inserted into the bore 454 in a direction Z substantially axially and colinear with bore axis 455 until the proximal end 490A abuts the end cap 456 of the stack assembly 450 in order to electrically couple each of the lead contacts 494 with a corresponding one of the connectors 400 of the stack assembly 450.

As described herein, in some examples, the attachment portion 416 of each connector housing 410 of the stack assembly 450 includes the attachment hole 418 within the attachment portion 416, which is sized and shaped to accept one of the feedthrough wires 480 within the attachment hole 418. In some examples, the number of attachment portions 416 of the connector housings 410 of the stack assembly 450 corresponds to the number of the feedthrough wires 480 of the header 474 of the implantable medical device 470. In further examples, the number of attachment portions 416 of the connector housings 410 of the stack assembly 450 corresponds to the number of the lead contacts 494 of the lead 490 of the implantable medical device 470. In some examples, the attachment holes 418 of each of the connector housings 410 of the stack assembly include the attachment hole axes 419 offset from and non-parallel to the bore hole axes 415. In some examples, the bore hole axis 415 of each of the connector housings 410 of the stack assembly 450 is substantially perpendicular to the attachment hole axis 419 of each of the connector housings 410 of the stack assembly 450.

As described herein, in some examples, the connectors 400 of the stack assembly 450 each include springs 430, with one spring 430 disposed within the bore hole 414 of the bore portion 412 of each of the connector housings 410 of the stack assembly 450. In some examples, each of the springs 430 are configured to electrically couple to one of the lead contacts 494 with the lead 490 disposed within each of the bore holes 414. In some examples, each of the springs 430 is disposed circumferentially around the bore hole 414 of each of the connector housings 410. In further examples, each of the springs 430 is configured to abut and electrically couple to a different one of the lead contacts 494 with the portion of the lead 490 disposed within the bore 454 of the stack assembly 450.

In this way, in some examples, all weld points of the one or more stack assemblies 450 to the feedthrough wires 480 are easily accessible from above (as seen in FIG. 9) without requiring large amounts of space around the one or more stack assemblies 450. Moreover, because the weld points can be positioned close to the housing 472 of the implantable medical device 470, routing operations for the feedthrough wires 480 can be reduced, if not eliminated, in comparison to the positioning of weld points of conventional connectors which is on the sides of the conventional connector housings, as shown in FIG. 3. Also, in some examples, the ease of access of the weld points and the substantially axial welding along the direction Y (FIG. 5B) enables automation of the welding process. Also, in some examples, each of the weld points including the feedthrough wire disposed within the attachment hole 418 provides for a stable junction, which, in turn, provides for better weld joints, at least because the attachment hole 418 provides for captivation and retention of the corresponding feedthrough wire 480 prior to, during, and/or following the welding operation. In this way, there is little to no movement between the attachment hole 418 and the corresponding feedthrough wire 480 during the welding process and afterward while the weld joint cools. In comparison, welding of feedthrough wires to conventional connectors (FIG. 3) does not captivate the feedthrough wire, thereby allowing movement between the connector and the corresponding feedthrough wire before, during, and after the welding process without some additional constraints added during the process in the form of tooling, jigs, or the like. Restraining movement after welding is especially important due to relaxation of stresses in the feedthrough wires during cooling which can cause the feedthrough wires to pull away from the connector and the weld thereto without proper constraint. In some examples, the stability of the present weld joints before, during, and after the substantially axial welding operation further facilitates automated welding in addition to improving weld quality.

The present inventors have recognized various advantages of the subject matter described herein. The present inventors have recognized, among other things, that the present subject matter can be used to allow connectors within an implantable medical device to be closer to the hermetic electronic enclosure of the device, thereby potentially reducing the wire routing operations within a header of the device and reducing the free space needed in the header to allow for the welding of feedthrough wires to the connectors. Also, the present subject matter is advantageous in that it is conducive to automatization of processes for the attachment of the connectors to the feedthrough wires, at least in part due to the enhanced welding junctions. In various examples, the present subject matter is advantageous in that it provides a more reliable and simpler-to-manufacture design for the header of the device. While various advantages of the example systems are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A connector for an implantable medical device, the connector configured to accept a lead therein and electrically couple to a lead contact of the lead, the implantable medical device including a feedthrough wire extending from a housing, the connector comprising:
   a connector housing disposed completely outside of the housing of the implantable medical device, the connector housing including:
      a bore portion including a bore hole therethrough, the bore hole including a bore hole axis, the bore hole being sized and shaped to accept the lead within the bore hole; and
      an attachment portion coupled to the bore portion, wherein the attachment portion and the bore portion are unitary, the attachment portion including an attachment hole within the attachment portion sized and shaped to accept the feedthrough wire within the attachment hole, the attachment hole including an attachment hole axis offset from and non-parallel to the bore hole axis.

2. The connector of claim 1, wherein the bore portion is substantially cylindrical.

3. The connector of claim 1, comprising a spring disposed within the bore hole of the bore portion, the spring configured to electrically couple to the lead contact with the lead disposed within the bore hole.

4. The connector of claim 1, wherein the attachment portion extends outwardly from the bore portion.

5. The connector of claim 1, wherein the bore hole axis is substantially perpendicular to the attachment hole axis.

6. The connector of claim 1, comprising a seal coupled to the bore portion, the seal configured to sealingly engage with the lead with the lead disposed within the bore hole.

7. A stack assembly for an implantable medical device, the stack assembly configured to accept a lead therein and electrically couple to at least two lead contacts of the lead, the implantable medical device including at least two feedthrough wires extending from a housing, the stack assembly comprising:
   at least two connector housings including a first connector housing and a second connector housing, each of the connector housings disposed completely outside of the housing of the implantable medical device and including:
      a bore portion including a bore hole therethrough, the bore hole including a bore hole axis, the bore hole being sized and shaped to accept the lead within the bore hole; and
      an attachment portion coupled to the bore portion, wherein the attachment portion and the bore portion are unitary, the attachment portion including an attachment hole within the attachment portion sized and shaped to accept one of the feedthrough wires within the attachment hole, the attachment hole including an attachment hole axis offset from and non-parallel to the bore hole axis, wherein the bore hole axes of the at least two connector housings are colinear; and
   at least one seal disposed between the first connector housing and the second connector housing, the seal configured to sealingly engage with the lead with the lead disposed within the bore holes of the first connector housing and the second connector housing.

8. The stack assembly of claim 7, wherein the bore portion of each of the first connector housing and the second connector housing is substantially cylindrical.

9. The stack assembly of claim 7, comprising at least two springs with one spring disposed within the bore hole of the bore portion of each of the first connector housing and the second connector housing, each of the springs configured to electrically couple to one of the lead contacts with the lead disposed within each of the bore holes.

10. The stack assembly of claim 7, wherein the attachment portion of each of the connector housings extends outwardly from the bore portion.

11. The stack assembly of claim 7, wherein the bore hole axis of each of the connector housings is substantially perpendicular to the attachment hole axis.

12. The stack assembly of claim 7, wherein the bore holes of the at least two connector housings form a bore within the stack assembly, the bore sized and shaped to accept a portion of the lead within the bore.

13. The stack assembly of claim 12, comprising at least two springs with one spring disposed within the bore hole of the bore portion of each of the first connector housing and the second connector housing, each of the springs configured to electrically couple to one of the lead contacts with the lead disposed within the bore hole.

14. The stack assembly of claim 13, wherein one of the at least two springs is disposed circumferentially around the bore hole of each of the at least two connector housings, each of the at least two springs being configured to abut and electrically couple to a different one of the at least two lead contacts with the portion of the lead disposed within the bore of the stack assembly.

15. A stack assembly for an implantable medical device, the stack assembly configured to accept a lead therein and electrically couple to a plurality of lead contacts of the lead, the implantable medical device including a plurality of feedthrough wires extending from a housing, the stack assembly comprising:
   a plurality of connector housings corresponding to the plurality of lead contacts of the lead, each of the plurality of connector housings disposed completely outside of the housing of the implantable medical device and including:

a bore portion including a bore hole therethrough, the bore hole including a bore hole axis, the bore hole being sized and shaped to accept the lead within the bore hole; and an attachment portion coupled to the bore portion, wherein the attachment portion and the bore portion are unitary, the attachment portion including an attachment hole within the attachment portion sized and shaped to accept one of the plurality of feed-through wires within the attachment hole, the attachment hole including an attachment hole axis offset from and non-parallel to the bore hole axis, wherein the bore hole axes of the plurality of connector housings are colinear;

a plurality of seals with one seal of the plurality of seals disposed between each pair of adjacent connector housings of the plurality of connector housings, each of the plurality of seals being configured to sealingly engage with the lead with the lead disposed within the bore holes of the plurality of connector housings; and a plurality of springs with one spring disposed within the bore hole of the bore portion of each of the plurality of connector housings, each of the springs configured to electrically couple to one of the plurality of lead contacts with the lead disposed within each of the bore holes, wherein the bore holes of the plurality of connector housings form a bore within the stack assembly, the bore sized and shaped to accept a portion of the lead within the bore.

16. The stack assembly of claim 15, wherein the bore portion of each of the plurality of connector housings is substantially cylindrical.

17. The stack assembly of claim 15, wherein the attachment portion of each of the connector housings extends outwardly from the bore portion.

18. The stack assembly of claim 15, wherein the bore hole axis of each of the connector housings is substantially perpendicular to the attachment hole axis.

19. The stack assembly of claim 15, wherein one of the plurality of springs is disposed circumferentially around the bore hole of each of the plurality of connector housings, each of the plurality of springs being configured to abut and electrically couple to a different one of the plurality of lead contacts with the portion of the lead disposed within the bore of the stack assembly.

20. The stack assembly of claim 15, wherein each seal of the plurality of seals is substantially ring-shaped and formed of a resilient material to seal around the lead disposed within the bore of the stack assembly.

\* \* \* \* \*